United States Patent
Awazu et al.

[11] Patent Number: 5,475,112
[45] Date of Patent: Dec. 12, 1995

[54] METHOD FOR PRODUCING SUBSTITUTED PYRIDINE DERIVATIVES

[75] Inventors: Takao Awazu; Hiroshi Okada; Masamitsu Matsumoto, all of Kusatsu, Japan

[73] Assignee: Ishihara Sangyo Kaisha Ltd., Osaka, Japan

[21] Appl. No.: 317,774

[22] Filed: Oct. 4, 1994

Related U.S. Application Data

[63] Continuation of Ser. No. 117,359, Sep. 7, 1993, abandoned, which is a continuation of Ser. No. 877,248, May 1, 1992, abandoned.

[30] Foreign Application Priority Data

May 2, 1991 [JP] Japan ................................ 3-196221
Dec. 20, 1991 [JP] Japan ................................ 3-361132

[51] Int. Cl.$^6$ .................................................. C07D 211/38
[52] U.S. Cl. .................................................. 546/346
[58] Field of Search ........................................ 546/346

[56] References Cited

U.S. PATENT DOCUMENTS

| | | | |
|---|---|---|---|
| 4,260,766 | 4/1981 | Morris | 546/303 |
| 5,037,824 | 8/1991 | Takasugi et al. | 546/279 |

FOREIGN PATENT DOCUMENTS

| | | |
|---|---|---|
| 2333797 | 1/1974 | Germany . |
| 56-43268 | 4/1981 | Japan . |
| 58-121271 | 7/1983 | Japan . |

OTHER PUBLICATIONS

Chem Abstracts vol. 95, 1981 p. 635 #95:97603w "6-Chloro-2-(Chloromethyl)Pyridines".
World Patents Index Latest, Week 9009, AN 90-065844, & SU-A-1479427, May 15, 1989, "Glass Composition Comprise Oxide Silicon Boron Aluminium Magnesium Calcium Strontium Barium".
Patent Abstracts of Japan, vol. 12, No. 301(C-521), Aug. 16, 1988, & JP-A-63-074935, Apr. 5, 1988, "Glass Composition for Substrate, Having Improved Chemical Resistance".
Chemical Abstracts, vol. 90, No. 26, Jun. 25, 1979, No. 208890F, p. 312, V. Nikulin, et al., "Heat-Resistant Glass".
Chemical Abstracts, vol. 102, No. 8, Feb. 25, 1985, No. 66289G, p. 263, "Acid Resistant Barium Silicate Glass".
World Patents Index Latest, Week 8532, An 85-192599, & JP-A-60-118648, Jun. 26, 1985, "Glaze Composition Ceramic Substrate Contain Oxide Silicon Aluminium Boron Calcium Barium Strontium".

*Primary Examiner*—C. Warren Ivy
*Assistant Examiner*—D. Margaret M. Mach
*Attorney, Agent, or Firm*—Oblon, Spivak, McClelland, Maier & Neustadt

[57] ABSTRACT

A method for producing a substituted pyridine derivative of the formula (II):

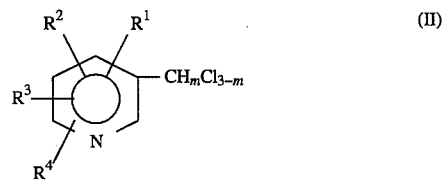

wherein each of $R^1$, $R^2$, $R^3$ and $R^4$ is a hydrogen atom, a halogen atom or an alkyl group, and m is an integer of from 1 to 3, which comprises reducing a substituted trichloromethylpyridine derivative of the formula (I):

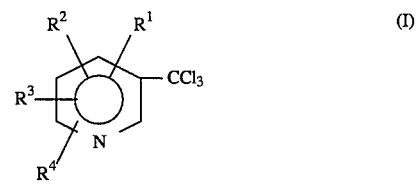

wherein $R^1$, $R^2$, $R^3$ and $R^4$ are as defined above, with use of acetic acid, hydrochloric acid or sulfuric acid, as a proton donor, and zinc, tin or a mixture thereof, as a reducing agent.

13 Claims, No Drawings

METHOD FOR PRODUCING SUBSTITUTED PYRIDINE DERIVATIVES

This application is a continuation of application Ser. No. 08/117,359, filed on Sep. 7, 1993 now abandoned, which is a continuation of 07/877,248 filed May 1, 1992 now abandoned.

The present invention relates to a method for producing substituted pyridine derivatives of the following formula (II), such as 2-chloro-5-chloromethylpyridine (hereinafter referred to simply as CCMP) and 2-chloro-5-dichloromethylpyridine (hereinafter referred to simply as CDCP), which are useful as intermediate materials for e.g. agricultural chemicals or pharmaceuticals:

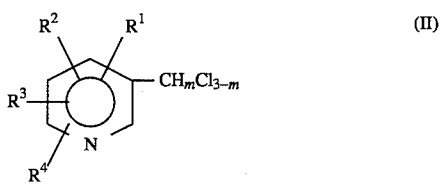

wherein m is an integer of from 1 to 3, and each of $R^1$, $R^2$, $R^3$ and $R^4$ is a hydrogen atom, a halogen atom or an alkyl group.

Various proposals have been made with respect to methods for producing substituted pyridine derivatives of the formula (II). For example, methods for producing CCMP have been proposed in U.S. Pat. Nos. 4,778,896, 4,990,622, and 4,958,025. However, these methods have drawbacks such that it is rather difficult to obtain starting materials for industrial operation, or the reaction process is rather long. Further, methods for producing CDCP have been proposed in U.S. Pat. Nos. 4,205,175, 4,241,213, 5,051,513 and 4,497,955. However, these methods also have various problems for industrial application, such that the yield of CDCP is low, the reaction process is long, or it is difficult to separate CDCP from by-products formed. On the other hand, importance of CCMP, CDCP and the like has recently been increased as intermediates for the production of insecticides of nitromethylene derivatives, and it is desired to develop a method for producing them, which is suitable for industrial application. The present inventors have conducted various studies on a method for producing substituted pyridine derivatives of the above formula (II) including CCMP and CDCP. As a result, they have found it possible to obtain the substituted pyridine derivatives of the formula (II) including CCMP and CDCP, selectively, by reducing substituted trichloromethylpyridine derivatives of the following formula (I) which are obtainable in large amounts relatively inexpensively, with use of a certain specific proton donor and reducing agent. The present invention has been accomplished on the basis of this discovery.

Thus, the present invention provides a method for producing a substituted pyridine derivative of the formula (II):

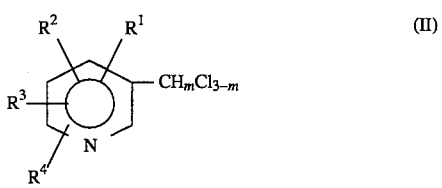

wherein each of $R^1$, $R^2$, $R^3$ and $R^4$ is a hydrogen atom, a halogen atom or an alkyl group, and m is an integer of from 1 to 3, which comprises reducing a substituted trichloromethylpyridine derivative of the formula (I):

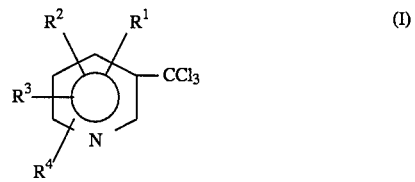

wherein $R^1$, $R^2$, $R^3$ and $R^4$ are as defined above, with use of acetic acid, hydrochloric acid or sulfuric acid, as a proton donor, and zinc, tin or a mixture thereof, as a reducing agent.

Now, the present invention will be described in detail with reference to the preferred embodiments.

With respect to $R^1$, $R^2$, $R^3$ and $R^4$ in the formulas (I) and (II), the halogen atom may be a fluorine atom, a chlorine atom, a bromine atom or an iodine atom, and the alkyl group may be a $C_{1-6}$ alkyl group such as a methyl group, an ethyl group, a propyl group, a butyl group, a pentyl group or a hexyl group. Each of such alkyl groups includes straight chain and branched aliphatic chain structural isomers.

The substituted trichloromethylpyridine derivative of the formula (I) as the starting material for the method of the present invention, may, for example, be 3-trichloromethylpyridine; a halogen-substituted trichloromethylpyridine such as 2-chloro-3-trichloromethylpyridine, 2- or 3-chloro-5-trichloromethylpyridine, 2-chloro-3-fluoro-5-trichloromethylpyridine, 2,5-dichloro-3-trichloromethylpyridine, 2,6-dichloro-3-trichloromethylpyridine, 2,3-difluoro-5-trichloromethylpyridine, 2,3-dichloro-5-trichloromethylpyridine, 2-bromo-3-fluoro-5-trichloromethylpyridine, 2-fluoro-5-trichloromethylpyridine or 2,3,6-trichloro-5-trichloromethylpyridine; or an alkyl-substituted trichloromethylpyridine such as 2-methyl-3-trichloromethylpyridine, 3-methyl-5-trichloromethylpyridine or 2-methyl-5-trichloromethylpyridine.

These derivatives can readily be prepared in accordance with conventional methods, for example, the methods disclosed in publications such as Japanese Unexamined Patent Publications No. 22617/1980, No. 76860/1980 and No. 115776/1981 and U.S. Pat. Nos. 4,504,665, 4,288,599 and 4,241,213 or in literatures such as J. Med. Chem. Vol. 13, p. 1124–1130 (1970), and Chem. Pharm. Bull. Vol 38, p. 2246–2258 (1990), or by a proper combination or modification of these methods.

The compound obtained by the method of the present invention i.e. the substituted pyridine derivative of the formula (II), may, for example, be 3-dichloromethylpyridine; 3-chloromethylpyridine; 3-methylpyridine; a halogen-substituted dichloromethylpyridine such as 2-chloro-3-dichloromethylpyridine, 2- or 3-chloro-5-dichloromethylpyridine, 2-chloro-3-fluoro-5-dichloromethylpyridine, 2,5-dichloro-3-dichloromethylpyridine, 2,6-dichloro-3-dichloromethylpyridine, 2,3-difluoro-5-dichloromethylpyridine, 2,3-dichloro-5-dichloromethylpyridine, 2-fluoro-5-dichloromethylpyridine, 2-bromo-3-fluoro-5-dichloromethylpyiridine or 2,3,6-trichloro-5-dichloromethylpyridine; a halogen-substituted chloromethylpyridine such as 2-chloro-3-chloromethylpyridine, 2- or 3-chloro-5-chloromethylpyridine, 2-chloro-3-fluoro-5-chloromethylpyridine, 2,5-dichloro-3-chloromethylpyridine, 2,6-dichloro-3-chloromethylpyridine, 2,3-difluoro-5-chloromethylpyridine, 2-bromo-3-fluoro-5-chloromethylpyridine, 2-fluoro-5-chloromethylpyridine, 2,3-dichloro-5-chloromethylpyridine or 2,3,6-trichloro-5-chloromethylpyridine; a halogen-substituted methylpyridine such as 2-chloro-3-methylpyridine, 2- or 3-chloro-5-methylpyridine, 2-chloro-3-fluoro-5-methylpyridine, 2,5-dichloro-3-methylpyridine, 2,6-dichloro-3-methylpyridine, 2,3-difluoro-5-methylpyridine, 2,3-dichloro-5-methylpyridine, 2-fluoro-5-methylpyridine, 2-bromo-3-fluoro-5-methylpyridine or 2,3,6-trichloro-5-methylpyridine; an alkyl-substituted dichloromethylpyridine such as 5-dichloromethyl-2-methylpyridine, 5-dichloromethyl-3-methylpyridine or 3-dichloromethyl-2-methylpyridine; an alkyl-substituted chloromethylpyridine such as 5-chloromethyl-2-methylpyridine, 5-chloromethyl-3-methylpyridine or 3-chloromethyl-2-methylpyridine; or an alkyl-substituted methylpyridine such as 2,3-dimethylpyridine, 2,5-dimethylpyridine or 3,5-dimethylpyridine.

The proton donor to be used for the method of the present invention, may be acetic acid, hydrochloric acid or sulfuric acid. Preferred is sulfuric acid or acetic acid. More preferred is sulfuric acid. The reducing agent may be zinc, tin or a mixture thereof. Preferred is zinc. The shape of zinc or tin as the reducing agent may be suitably selected depending upon the actual operation, and it may be powder-like, sand-like, turning, granule-like, grain-like, mossy, plate-like or stick.

In the reduction reaction of the present invention, it may sometimes happen that substances differing in the degree of the reduction reaction are contained in the product. Namely, two or three types of substances having the trichloromethyl group in the substituted trichloromethylpyridine derivative as the starting material converted to a dichloromethyl group, a chloromethyl group or a methyl group, may sometimes be contained simultaneously in the product. Therefore, in the method of the present invention, the amounts of the proton donor and the reducing agent relative to the substituted trichloromethylpyridine derivative as the starting material are selected so that the desired product is contained in a large amount in the reaction product. It is difficult to define such amounts generally. However, the proton donor is usually from 1 to 20 equivalent, and the reducing agent is usually from 1 to 20 equivalent, relative to the substituted trichloromethylpyridine derivative as the starting material. These amounts vary depending upon the desired products, and will be explained independently with respect to the respective desired products. Usually, the amounts of use suitable for the starting materials, the desired products and the reaction conditions are determined by a preliminary experiment in small scale, and then will be applied to an industrial operation. When the desired products are dichloromethylpyridines (the formula (II) wherein m is 1), the proton donor is from 1 to 10 equivalent, preferably from 1 to 3 equivalent, and the reducing agent is from 1 to 10 equivalent, preferably from 1 to 3 equivalent. When the desired products are chloromethylpyridines (the formula (II) wherein m is 2), the proton donor is from 2 to 15 equivalent, preferably from 2 to 4 equivalent, and the reducing agent is from 2 to 15 equivalent, preferably from 2 to 4 equivalent. When the desired products are methylpyridines (the formula (II) wherein m is 3), the proton donor is from 3 to 20 equivalent, preferably from 3 to 6 equivalent, and the reducing agent is from 3 to 20 equivalent, preferably from 3 to 6 equivalent. If the proton donor or the reducing agent departs substantially from such a range, there will be drawbacks such that the desired reaction does not proceed, the amount will be more than necessary, thus leading to an economical loss, or by-products tend to be substantial, whereby the yield tends to be low, or the costs tend to be high.

In the reduction reaction of the present invention, the solvent may be present or may not be present. As the solvent to be used, an alcohol, a nitrile, an ether, a halogenated hydrocarbon, a ketone, an ester, an aprotic polar solvent may be mentioned. An alcohol such as methanol, ethanol or propanol is preferred. Among them, methanol is particularly preferred. The amount of the solvent is usually from 0 to 100 parts by weight, preferably from 0.5 to 50 parts by weight, relative to one mol of the substituted trichloromethylpyridine derivative as the starting material. If the amount of the solvent exceeds the above range substantially, the costs tend to be high, such being undesirable. When sulfuric acid is used as the proton donor, it is usually preferred to employ an alcohol, particularly methanol.

The reaction temperature for the reduction reaction of the present invention, varies depending upon the types of the starting material, the desired product, the reducing agent, the proton donor and the solvent and other reaction conditions and can not be generally defined. However, it is usually within a range of from $-78°$ C. to $+200°$ C., preferably from $-20°$ C. to $+100°$ C. The reaction time is usually from 0.1 to 50 hours, preferably from 0.5 to 20 hours. In the present invention, the starting material, the proton donor and the reducing agent may be added in a suitable manner e.g. all at once or in a divided fashion. However, the proton donor and the reducing agent are preferably added in a divided fashion.

From the reaction product of the reduction process of the present invention, the desired product can readily be obtained by a usual purification and separation method. For example, the reaction mixture may be put into water, and if necessary, the desired product may be separated by extraction or distillation. Further, after separation of the desired product from the reaction mixture, an unreacted starting material or an intermediate product of the reduction reaction may be recycled for use in the reduction reaction.

Now, the present invention will be described in further detail with reference to Examples. However, it should be understood that the present invention is by no means restricted to such specific Examples.

EXAMPLE 1

2.31 g (0.01 mol) of 2-chloro-5-trichloromethylpyridine (heneinafter CTC) was dissolved in 15 ml of concentrated hydrochloric acid, and then 2.85 g (2.4 equivalent) of tin powder was added, and the mixture was reacted at room temperature for 30 minutes and at 70° C. for 50 minutes under stirring.

After completion of the reaction, the reaction mixture was analyzed by gas chromatography, whereby the composition was found to be 74.3% of 2-chloro-5-chloromethylpyridine (hereinafter CCMP), 21.3% of 2-chloro-5-dichloromethylpyridine (hereinafter CDCP) and 4.4% of others. The reaction mixture was poured into 100 ml of water and extracted three times with 100 ml of diethyl ether, and the extract was dried over anhydrous sodium sulfate and evaporated. The residue was purified by silica gel column chromatography (developing solvent: n-hexane/ethyl acetate= 15/l) to obtain 0.49 g of CCMP having a melting point of from 37° to 38° C.

NMR ($\delta$: 60MHz, CDCl$_3$) 8.42(1H,d,J=3 Hz), 7.67(1H, dd,J=8, 3Hz), 7.33(1H,d,J=8 Hz), 4.58(2H,s)

EXAMPLE 2

30.7 g (3 equivalent) of concentrated sulfuric acid was added to 400 ml of methanol, and then 46.2 g (0.2 mol) of CTC was added, and the mixture was thoroughly stirred to obtain a homogeneous solution. Then, while adding 31.4 g (2.4 equivalent) of zinc powder in a divided fashion in twelve portions over a period of three hours and fifteen minutes at a temperature of from 10° to 25° C., the reaction was conducted. After completion of the addition, the reaction was further continued at room temperature for 40 minutes under stirring.

After completion of the reaction, methanol was distilled off under reduced pressure from the reaction mixture, and 200 ml of water was poured into the reaction mixture and extracted with 200 ml of methylene chloride. Then, the aqueous layer was extracted twice with 100 ml of methylene chloride, and the extract was dried over 46.2 g of anhydrous sodium sulfate. The dried reaction mixture was analyzed by gas chromatography, whereby it was found to contain 84.3% of CCMP, 3.8% of CDCP and 11.4% of 2-chloro-5-methylpyridine (hereinafter CMP). Methylene chloride was distilled off, and then the residue was distilled under reduced pressure to obtain 21.47 g of CCMP as white crystals (purity: 85.0% as analyzed by gas chromatography).

EXAMPLE 3

While dropwise adding 3.0 g (5 equivalent) of acetic acid to a mixed solution containing 2.31 g (0.01 mol) of CTC, 1.57 g (2.4 equivalent) of zinc powder and 20 ml of methanol, at a temperature of from 20° to 33° C. over a period of 15 minutes, the reaction was conducted. After completion of the dropwise addition, the reaction was continued for further 30 minutes at the same temperature under stirring.

After completion of the reaction, the reaction mixture was poured into 100 ml of water and extracted twice with 100 ml of methylene chloride. The extract was washed with 100 ml of water, and dried over anhydrous sodium sulfate. The dried reaction mixture was analyzed by gas chromatography, whereby it was found to contain 69.0% of CCMP, 12.7% of CDCP, 16.3% of CMP, 0.5% of CTC and 1.5% of others. Methylene chloride was distilled off to obtain 1.46 g of CCMP (purity: 69% as analyzed by gas chromatography).

EXAMPLES 4 TO 13

Examples 4 to 13 conducted in the same manner as in Example 1 to 3 are shown in Table 1.

TABLE 1

| Example No. | Amount of CTC used (g) | Reducing agent Type, shape | Equivalent amount | Adding time (hr) | Number of added times | Proton donor Type | Equivalent amount | Solvent Type | Amount |
|---|---|---|---|---|---|---|---|---|---|
| 4 | 2.31 | Zinc, powder | 2.4 | 4.5 | 8 | Acetic acid | 2.1 | Methanol | 20 g |
| 5 | 2.31 | Zinc, powder | 2.4 | 1.5 | 12 | Acetic acid | 2.2 | Acetonitrile | 20 ml |
| 6 | 2.31 | Zinc, powder | 2.4 | 6 | 12 | Acetic acid | 2.2 | 1,4-dioxane | 20 ml |
| 7 | 2.31 | Zinc, powder | 2.4 | 1.5 | 12 | Acetic acid | 2.2 | Acetone | 20 ml |
| 8 | 2.31 | Zinc, sand-like | 2.4 | 8 | 6 | Acetic acid | 2.1 | Methanol | 20 g |
| 9 | 2.31 | Zinc, turning | 2.4 | 8 | 7 | Acetic acid | 2.1 | Methanol | 20 g |
| 10 | 2.31 | Zinc, powder | 2.7 | 2.5 | 9 | Sulfuric acid | 3 | Methanol | 50 ml |
| 11 | 2.31 | Zinc, powder | 2.4 | — | — | Acetic acid | 8 | Methanol | 20 ml |
| 12 | 2.31 | Zinc, powder | 2.2 | — | — | Acetic acid | 8 | Ethanol | 20 ml |
| 13 | 2.31 | Zinc, powder | 2.4 | — | — | Conc. hydrochloric acid | 8.6 | Methanol | 20 ml |

| Example No. | Amount of CTC used (g) | Reaction temp. (°C.) | Reaction time (hr) | Composition of the reaction product (%) | | | |
|---|---|---|---|---|---|---|---|
| | | | | CCMP | CDCP | CMP | CTC |
| 4 | 2.31 | 10–17 | 1 | 77.4 [67.8] | 0.4 | 10.5 | 0 |
| 5 | 2.31 | 18–28 | 16 | 47.1 | 0 | 28.5 | 0 |
| 6 | 2.31 | 17–27 | 1 | 32.0 | 20.9 | 0 | 5.8 |
| 7 | 2.31 | 18–22 | 13.5 | 22.0 | 0 | 14.9 | 0 |
| 8 | 2.31 | 20 | 16 | 71.7 | 3.7 | 8.8 | 0 |
| 9 | 2.31 | 20 | 16 | 62.2 | 15.6 | 11.5 | 0 |
| 10 | 2.31 | 5–24 | 1 | 87.8 [79.0] | 0 | 9.0 | 0 |

TABLE 1-continued

| 11 | 2.31 | 70 | 0.5 | 65.3* | tr* | 31.7* | 0* |
| 12 | 2.31 | 70 | 0.5 | 45.4 | 26.7 | 25.5 | 1.0 |
| 13 | 2.31 | 20–40 | 0.5 | 61.6 | 7.3 | 27.7 | 0.6 |

In Table 1, Examples 4 to 10 represent a method wherein the reducing agent is added at the final stage, and Examples 11 to 13 represent a method wherein the proton donor is added or dropwise added at the final stage. Example 11 represents a case where the proton donor was added all at once, and Examples 12 and 13 represent a case where the proton donor was dropwise added over a period of about 15 minutes.

In Table 1, the composition of the reaction product indicates the values measured by gas chromatography, and * indicates a value measured by gas chromatography of crude oil obtained by post-treatment after completion of the reaction. In the column for CCMP, the value in the bracket [] indicates the yield of CCMP as isolated by silica gel column chromatography.

EXAMPLE 14

To a suspension of 39.9 g of 2,6-dichloro-3-trichloromethylpyridine in 300 ml of methanol, 23.0 g of concentrated sulfuric acid was added. While adding 19.68 g of zinc powder at room temperature in a divided fashion in six portions over a period of 2.5 hours, the reaction was conducted. After completion of the addition, the reaction was continued at room temperature for two hours under stirring.

After completion of the reaction, the reaction mixture was analyzed by gas chromatography, whereby the composition was found to be 80.8% of 2,6-dichloro-3-chloromethylpyridine, 0.9% of 2,6-dichloro-3-dichloromethylpyridine and 12.5% of 2,6-dichloro-3-methylpyridine. The reaction mixture was poured into 300 ml of water and extracted three times with 300 ml of methylene chloride. The extract was dried over anhydrous sodium sulfate and evaporated. The residue was purified by silica gel column chromatography (developing solvent: n-hexane/ethyl acetate=30/1) to obtain 16.16 g of 2,6-dichloro-3-chloromethylpyridine having a melting point of from 79° to 83° C.

EXAMPLE 15

To 75 ml of a methanol solution containing 9.87 g of 2,3-dichloro-5-trichloromethylpyridine, 5.69 g of concentrated sulfuric acid was dropwise added. While adding 6.1 g of zinc powder at a temperature of from 5° to 30° C. in an ice bath over a period of 1.5 hours in a divided fashion in five times, the reaction was conducted. After completion of the addition, the reaction was continued at room temperature for one hour under stirring.

After completion of the reaction, the reaction mixture was poured into 120 ml of water and extracted three times with 200 ml of methylene chloride. The extract was dried over anhydrous sodium sulfate. The dried reaction mixture was analyzed by gas chromatography, whereby it was found to contain 84.1% of 2,3-dichloro-5-chloromethylpyridine and 12.0% of 2,3-dichloro-5-methylpyridine. Methylene chloride was distilled off, and then the residue was purified by silica gel column chromatography (developing solvent: n-hexane/ethyl acetate= 15/1) to obtain 4.65 g of 2,3-dichloro-5-chloromethylpyridine, having a melting point of from 39° to 41° C.

EXAMPLE 16

To 170 ml of a methanol solution containing 37.9 g (0.164 mol) of 2-chloro-3-trichloromethylpyridine, 25.2 g of concentrated sulfuric acid was added. While adding 25.7 g of zinc powder at a temperature of from 20° to 30° C. over a period of one hour in a divided fashion in many times, the reaction was conducted. After completion of the addition, the reaction was continued at a temperature of from 20° to 30° C. for 0.5 hour under stirring.

After completion of the reaction, the reaction mixture was analyzed by gas chromatography, whereby the composition was found to be 83.2% of 2-chloro-3-chloromethylpyridine, 2.3% of 2-chloro-3-dichloromethylpyridine and 11.9% of 2-chloro-3-methylpyridine. The reaction mixture was poured into 300 ml of water and extracted twice with 400 ml of methylene chloride. The extract was dried over anhydrous sodium sulfate and evaporated. The residue was purified by silica gel column chromatography (developing solvent: n-hexane/ethyl acetate= 15/1 to 5/1) to obtain 17.06 g of 2-chloro-3-dichloromethylpyridine having a melting point of from 35° to 36° C.

EXAMPLE 17

13.3 g (1.3 equivalent) of concentrated sulfuric acid was added to 200 ml of methanol, and then 23.1 g (0.1 mol) of CTC was added thereto, and the mixture was thoroughly stirred to obtain a homogeneous solution. Then, while adding 7.85 g (1.2 equivalent) of zinc powder at a temperature of from −5° C. to +4° C. over a period of one hour in a divided fashion in twelve times, the reaction was conducted. After completion of the addition, the reaction was continued at room temperature for 15 minutes under stirring.

After completion of the reaction, the reaction mixture was poured into 300 ml of water and extracted with 300 ml of methylene chloride. Then, the aqueous layer was extracted twice with 200 ml of methylene chloride, and the extract was dried over anhydrous sodium sulfate. The dried reaction mixture was analyzed by gas chromatography, whereby it was found to contain 83.9% of CDCP, 3.4% of CCMP and 7.7% of CTC. Methylene chloride was distilled off, and the residue was purified by silica gel column chromatography (developing solvent: n-hexane/ethyl acetate=15/1) to obtain 15.69 g of 2-chloro-5-dichloromethylpyridine.

EXAMPLES 18 TO 24

Examples 18 to 24 conducted in the same manner as in Examples 16 and 17 are shown in Table 2.

TABLE 2

| Example No. | Amount of CTC used (g) | Reducing agent | | | | Proton donor | | Solvent | |
|---|---|---|---|---|---|---|---|---|---|
| | | Type, shape | Equivalent amount | Adding time (hr) | Number of added times | Type | Equivalent amount | Type | Amount |
| 18 | 2.31 | Zinc, powder | 1.0 | — | 1 | Acetic acid | 8.0 | Methanol | 20 ml |
| 19 | 2.31 | Zinc, powder | 2.2 | 1 | 3 | Acetic acid | 2.1 | Ethyl acetate | 20 g |
| 20 | 2.31 | Zinc, powder | 2.4 | 3.5 | 6 | Acetic acid | 2.2 | 1,2-dichloroethane | 20 ml |
| 21 | 2.31 | Zinc, powder | 2.0 | — | 1 | 25 g of acetic acid | | | |
| 22 | 2.31 | Zinc, powder | 2.2 | 2 | 12 | Sulfuric acid | 1.0 | Methanol | 20 ml |
| 23 | 2.31 | Tin, powder | 2.4 | — | 1 | 15 ml of hydrochloric acid | | | |
| 24 | 2.31 | Zinc, powder | 1.4 | 2.5 | 7 | Sulfuric acid | 2.6 | Methanol | 20 ml |

| Example No. | Amount of CTC used (g) | Reaction temp. (°C.) | Reaction time (hr) | Composition of the reaction product (%) | | | |
|---|---|---|---|---|---|---|---|
| | | | | CDCP | CCMP | CMP | CTC |
| 18 | 2.31 | 70 | 1 | 48.1* | 8.4* | 6.0* | 35.9* |
| 19 | 2.31 | 20–23 | 1.5 | 46.0 | 14.4 | 20.0 | 0 |
| 20 | 2.31 | 20–70 | 20 | 26.7 | 22.5 | 0 | 13.0 |
| 21 | 2.31 | 50 | 4 | 42.5 | 30.2 | 17.8 | 5.9 |
| 22 | 2.31 | 18–25 | 18 | 35.2 | 28.2 | 0 | 0 |
| 23 | 2.31 | 20–33 | 2.5 | 64.2 [49] | 6.6 | 0 | 9.9 |
| 24 | 2.31 | 4–12 | 1 | 90.3* [76.3] | 8.0* | 0* | 0* |

In Table 2, the composition of the reaction product indicates the values measured by gas chromatography, and * indicates a value measured by gas chromatography of crude oil obtained by post-treatment after completion of the reaction. In the column for CDCP, the value in the bracket [] indicates the yield of CDCP isolated by silica gel column chromatography.

EXAMPLE 25

While adding 4.71 g of zinc powder at a temperature of from 20° to 33° C. over a period of 0.7 hour in a divided fashion in many times to a solution obtained by mixing 4.62 g of CTC, 4.59 g of sulfuric acid and 40 ml of methanol, the reaction was conducted. Further, the reaction was continued at room temperature for one hour and at 50° C. for 2.5 hours under stirring.

After completion of the reaction, the reaction mixture was analyzed by gas chromatography, whereby the composition was found to be 96.8% of CMP and 3.1% of CCMP. The reaction mixture was poured into 100 ml of water and extracted three times with 70 ml of methylene chloride. The extract was dried over anhydrous sodium sulfate and evaporated. The residue was purified by silica gel column chromatography (developing solvent: n-hexane/ethyl acetate= 15/l) to obtain 1.72 g of CMP.

EXAMPLES 26 AND 27

Examples 26 and 27 conducted in the same manner as in Example 25 are shown in Table 3.

TABLE 3

| Example No. | Amount of CTC used (g) | Reducing agent Type, shape | Equivalent amount | Adding time (hr) | Number of added times | Proton donor Type | Equivalent amount | Solvent Type | Amount |
|---|---|---|---|---|---|---|---|---|---|
| 26 | 2.31 | Zinc, powder | 2.6 | — | 1 | 19 g of Hydrochloric acid + 20 ml of water | | | |
| 27 | 23.1 | Zinc, powder | 2.75 | 0.7 | 6 | Sulfuric acid | 3.0 | Methanol | 400 ml |

| Example No. | Amount of CTC used (g) | Reaction temp. (°C.) | Reaction time (hr) | Composition of the reaction product (%) CMP | CCMP | CDCP | CTC |
|---|---|---|---|---|---|---|---|
| 26 | 2.31 | 30 | 0.7 | 61.7 | 3.7 | 0.7 | 0 |
| 27 | 23.1 | 18–40 | 1 | 64.1 | 35.9 | 0 | 0 |

In Table 3, the composition of the reaction product indicates the values measured by gas chromatography.

Substituted pyridine derivatives of the formula (II) obtained by the method of the present invention are useful as intermediate materials for agricultural chemicals or pharmaceuticals. For example, 2-chloro-5-chloromethylpyridine is useful for the production of an active compound for an insecticide shown in EP302389A or 163855A, and 2-chloro-5-dichloromethylpyridine is useful for the production of an active compound of an insecticide disclosed in U.S. Pat. Nos. 4,678,795 or 5,051,513.

We claim:

1. A method for producing a substituted pyridine derivative of the formula (II):

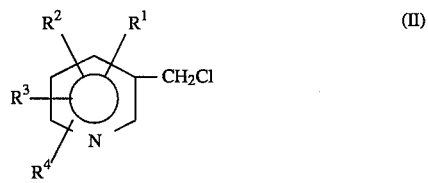

wherein each of $R^1$, $R^2$, $R^3$ and $R^4$ is a hydrogen atom a halogen atom or an $C_{1-6}$ alkyl group, which comprises:

reducing a substituted trichloromethylpyridine derivative of the formula (I):

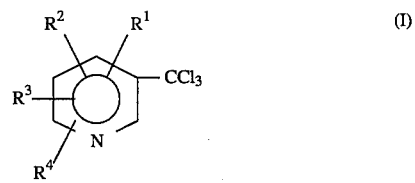

wherein $R^1$, $R^2$, $R^3$ and $R^4$ are as defined above, with hydrochloric acid or sulfuric acid, as a proton donor, zinc, as a reducing agent, and methanol, or ethanol as a solvent.

2. The method according to claim 1, wherein $R^1$, $R^2$, $R^3$ or $R^4$ in formulas (I) and (II) is a hydrogen atom or a halogen atom.

3. The method according to claim 1, wherein the substituted trichloromethylpyridine derivative of the formula (I) is 3-trichloromethylpyridine, 2-chloro-3-trichloromethylpyridine, 2-chloro-5-trichloromethylpyridine, 2,3-dichloro-5-trichloromethylpyridine or 2,6-dichloro-3-trichloromethylpyridine, and the substituted pyridine derivative of the formula (II) is 3-chloromethylpyridine; 2-chloro-3-chloromethylpyridine; 2-chloro-5-chloromethylpyridine; 2,3-dichloro-5-chloromethylpyridine; or 2,6-dichloro-3chloromethylpyridine.

4. The method according to claim 1, wherein the substituted trichloromethylpyridine derivative of the formula (I) is 2-chloro-5-trichloromethylpyridine or 2,3-dichloro-5-trichloromethylpyridine, and the substituted pyridine derivative of the formula (II) is 2-chloro-5-chloromethylpyridine or 2,3-dichloro-5-chloromethylpyridine.

5. The method according to claim 1, wherein the substituted trichloromethylpyridine derivative of the formula (I) is 2-chloro-5-trichloromethylpyridine, and the substituted pyridine derivative of the formula (II) is 2-chloro-5-chloromethylpyridine.

6. The method according to claim 1, wherein the solvent is methanol.

7. The method according to claim 1, wherein the reduction reaction is conducted at a reaction temperature of from −78° C. to +200° C.

8. The method according to claim 1, wherein the reduction reaction is conducted with from 1 to 20 equivalents of each of the proton donor and the reducing agent, relative to 1 mol of the substituted trichloromethylpyridine derivative of the formula (I).

9. The method according to claim 1, wherein the reduction reaction is conducted with up to 100 parts by weight of the solvent, relative to 1 mol of the substituted trichloromethylpyridine derivative of the formula (I).

10. The method according to claim 1, wherein 2-chloro-5-trichloromethylpyridine is reduced at a reaction temperature of from −20° C. to +100° C. with from 2 to 15 equivalents of the proton donor and from 2 to 15 equivalents of zinc, relative to 1 mol of 2-chloro-5-trichloromethylpyridine and from 0.5 to 50 parts by weight of the solvent, relative to 1 mol of 2-chloro-5-trichloromethylpyridine, to obtain 2-chloro-5-chloromethylpyridine.

11. The method according to claim 1, wherein 2-chloro-5-trichloromethylpyridine is reduced at a reaction temperature of from −20° C. to +100° C. with from 2 to 4 equivalents of the proton donor and from 2 to 4 equivalents of zinc, relative to 1 mol of 2-chloro-5-trichloromethylpyridine and from 0.5 to 50 parts by weight of the solvent, relative to 1 mol of 2-chloro-5-trichloromethylpyridine, to obtain 2-chloro-5chloromethylpyridine.

12. A method for producing 2-chloro-5-chloromethylpyridine, which comprises:

reducing 2-chloro-5-trichloromethylpyridine at a reaction temperature of from −20° C. to 100° C. in the presence of from 2 to 4 equivalents of sulfuric acid as the proton donor and from 2 to 4 equivalents of zinc, each relative to 1 mol of 2-chloro-5-trichloromethylpyridine, in from 0.5 to 50 parts by weight of methanol as the solvent.

13. A method for producing 2-chloro-5-chloromethylpyridine, which comprises:

reducing 2-chloro-5-trichloromethylpyridine at a reaction temperature of from −20° C. to 100° C. in the presence of from 2 to 4 equivalents of hydrochloric acid as the proton donor and from 2 to 4 equivalents of zinc, each relative to 1 mol of 2-chloro-5-trichloromethylpyridine in from 0.5 to 50 parts by weight of methanol as the solvent.

* * * * *